United States Patent [19]
LaFleur et al.

US005683706A

[11] Patent Number: 5,683,706
[45] Date of Patent: Nov. 4, 1997

[54] COSMETIC POWDER COMPOSITIONS HAVING IMPROVED SKIN COVERAGE

[75] Inventors: Patricia Alison LaFleur, Shrewsbury Township, Pa.; Leena Vadaketh, Newark, Del.; Jeffrey Keith Leppla, Baltimore, Md.

[73] Assignee: The Proctor & Gamble Company, Cincinnati, Ohio

[21] Appl. No.: 629,293

[22] Filed: Apr. 8, 1996

Related U.S. Application Data

[63] Continuation-in-part of Ser. No. 509,488, Jul. 31, 1995.

[51] Int. Cl.$^6$ ...................................................... A61K 7/00
[52] U.S. Cl. ............................................... 424/401; 424/63
[58] Field of Search ........................... 424/63, 401, 486, 424/489

[56] References Cited

U.S. PATENT DOCUMENTS

| | | | |
|---|---|---|---|
| 5,073,364 | 12/1991 | Giezendanner et al. | 424/63 |
| 5,283,062 | 2/1994 | Elliott et al. | 424/401 |
| 5,518,728 | 5/1996 | Burdzy | 424/401 |

FOREIGN PATENT DOCUMENTS

| | | |
|---|---|---|
| 0191292 | 1/1986 | European Pat. Off. . |
| 0191292 | 8/1986 | European Pat. Off. . |
| 62-016410 | 1/1987 | Japan . |
| 62-181210 | 8/1987 | Japan . |
| 9103076B | 5/1991 | Rep. of Korea . |
| 9103103B | 5/1991 | Rep. of Korea . |

OTHER PUBLICATIONS

Todd et al., "Volatile Silicone Fluids for Cosmetic Formulations", *Cosmetics and Toiletries*, vol.91, pp. 29–32 (1976).

*Primary Examiner*—Thurman K. Page
*Assistant Examiner*—Sharon Howard
*Attorney, Agent, or Firm*—John M. Howell; David L. Suter; Jacobus C. Rasser

[57] ABSTRACT

The present invention is for powder compositions containing high levels of talc, low levels of titanium dioxide and a sebum absorbing material wherein the composition has improved skin coverage, uniformity and duration of wear. The invention can be used in formulating numerous cosmetic powder compositions such as eye shadow, foundation, loose powder and the like.

20 Claims, No Drawings

COSMETIC POWDER COMPOSITIONS HAVING IMPROVED SKIN COVERAGE

This is a continuation-in-part of application Ser. No. 08/509,488, filed on Jul. 31, 1995.

TECHNICAL FIELD

The present invention is for powder compositions with improved skin coverage and uniformity and duration of wear compared to previously formulated compositions. These compositions comprises high levels of selected talc, little or no titanium dioxide as a filler or extender and a sebum absorbing material. Said compositions can be formulated to form a variety of color cosmetic compositions including eye shadows, foundations and the like.

BACKGROUND OF THE INVENTION

Color powder compositions for application to the skin, particularly the face and around the eyes are well known in the art. These compositions take a number of different forms ranging from loose powders in canisters to those that are molded or compressed into cakes and inserted into mirrored compact cases, typically supplied with an applicator, usually a pad, a puff or other implement.

These compositions comprise, in a major part, fillers and extenders, most of which are of the mineral variety. Examples of such mineral fillers and extenders include talc, kaolin, mica, silicon dioxide, silicon dioxide-coated mica and talc, titanium dioxide, titanium dioxide-coated mica and talc, fluroite, apatite, perlite, boron nitride and the like. To a lesser degree, such cosmetic powders include organic materials such as nylon and polyethylene. All these materials are blended together in various levels in order to impart desired benefits such as spreadibility and adherence while being smooth, lustrous and of high covering power.

Titanium dioxide, or $TiO_2$ is well known for use in the art as a filler or extender. Japanese Patent Application 62-16410, published Jan. 24, 1987, Pola Kasei Kogyo K K, discloses a combination of plate-like powders and globular $TiO_2$ having an average diameter 1–50 microns compounded in a solid cosmetic composition at a level from about 1% to 85%. Said cosmetic compositions are reputed to have excellent adherence to and smoothly spread on the skin. Japanese Patent Application 62-181210, published Aug. 8, 1987, Pola Kasei Kogyo K K, discloses solid cosmetic compositions comprising 10 to 85% of a base agent comprising plate shaped powders such as mica and talc with $TiO_2$ having average grain size of 1–50 microns in a ratio of powder to $TiO_2$ of 1:9 to about 9.5:0.5. The cosmetic compositions disclosed therein are reputed to have good adhesion and removal, good spread ability and good skin feel. Korean Patent Application 91-03133, published May 18, 1991, Lucky Company, discloses make-up compositions containing powders obtained by adsorbing 10–40% by weight of $TiO_2$ onto mica. Said treated mica is combined with 0.5–20% focus powders to form a emulsified foundation composition. Said composition is reputed to have a good soft focus effect and an ultraviolet ray intercepting effect. European Patent Application 0 191 292, published Aug. 20, 1986, Sumitomo Chemical, discloses makeup compositions comprising flaky titanium oxide having a mean thickness from 0.01 to below 0.1 microns and a mean thickness of 0.1 to 3 microns and a mean size of 0.8 to 70 microns. Said compositions disclosed therein include powder foundations wherein the titanium dioxide is used as an extender (as opposed to a pigment) at levels from about 20 to 90% by weight of the composition. Such foundations, containing about 50% titanium oxide, are reputed to be superior in terms of adherence and smooth feel to foundations containing comparable amounts of talc.

In the present invention, good coverage and uniformity on the skin is achieved utilizing selected talcs as opposed to titanium dioxide as the filler. Minimizing or eliminating titanium dioxide as a filler is advantageous since its presence generally is responsible for whitened or ashy look it leaves on the skin. This result is surprising based on comparison with compositions, such us pressed powders, containing high levels of non-specific talc that do not provide adequate coverage.

SUMMARY OF THE INVENTION

The present invention are for powder cosmetic composition comprising talc wherein said talc comprises:

a. a first talc having a particle size distribution wherein no more than about 45% of the particles are 10 microns or less; no more than about 70% of the particles are 15 microns or less and no more than about 85% of the particles are 20 microns or less;

b. a second talc having a particle size distribution wherein no less than about 55% of the particles are 10 microns or less, no less than about 80% of the particles are 15 microns or less and no less than about 90% of the particles are 20 microns or less; and c. a sufficient amount of an sebum absorbing material which absorbs from about 0.2 grams of sebum per gram of material (g/g) to about 3.5 g/g;

wherein the ratio of said first talc to said second talc is from about 1:1 to about 6:1.

One object of the present invention is to provide powder compositions which deliver significantly improved coverage and uniformity and duration of wear when applied to the skin. It is also an object of the present invention that the present invention provides compositions having a natural look to the skin, i.e. not whitened or ashy. Lastly an object of the present invention is to provide a convenient product form which delivers the benefits described above.

DETAILED DESCRIPTION OF THE INVENTION

Definitions

As used here "powder cosmetic composition" refer to any cosmetic composition that has less than about 20% liquid content in its packaged form.

As used heroin "pressed powder compositions" refer to any cosmetic composition whose packaged form is made by compressing the materials comprising a sufficient binder by physical means whereby a cake is formed having sufficient hardness to sustain its shape and resist crumbling. Said compositions are often formed in small shallow metal pans or godets to facilitate storage and placement into cosmetic cases.

As used herein "loose powder" refers to powder cosmetic composition absent the binder mentioned above, packaged in a loose form in cosmetic canisters. The canisters typically have a fine mesh screen over the loose powder wherein an applicator is applied to the screen to pick up the powder composition.

As used herein "powder foundations" refer to a cosmetic composition used for full face coverage similar to a cosmetic liquid foundation. The foundation provides an adherent base for other cosmetics such as blusher, rouge and powder.

As used herein "concealer" refers to a cosmetic composition used to conceal or hide imperfections on the face.

As used herein "packed density" refers to the density of the a material as measured by a Hosokawa Powder Characteristics Tester from Hosokawa Micron Corporation, Summit N.J., using the packed or packed method disclosed in The Annual Book of ASTM Standards, 1986, Section 5; incorporated herein by reference.

Talc

It has now been found that an improved coverage powder cosmetic composition can be achieved with high levels of talc selected based on its particle size distribution or PSD. These compositions provide coverage benefits previously not thought possible absent sufficient levels of other components such as titanium dioxide.

Talc is generally known to those skilled in the art as natural, powdered hydrous magnesium silicate. Talc can be ground into various particle sizes and acts as an anti caking agent that has a very smooth feel on the skin. Talc is available from a number of commercial suppliers such as Whittaker, Clark and Daniels Inc., South Plainfield N.J.; Cyprus Industrial Minerals Company, Englewood, Colo.; Presperse Inc., South Plainfiled N.J.; and L. A. Salamon, Inc., Nontville, N.J.; U.S. Cosmetics, Dayville, Conn.; Miki America, Inc., Dayville, Conn.; Ultra Chemical, Inc., Red Band, N.J.; Color Technologies, South Plainfield, N.J.; Kobo Products, Inc., South Plainfield, N.J.; Charles B. Chrystal Co., Inc., New York, N.Y. and Ecco Resources, So. Plainfield, N.J. Compositions of the present invention comprise from about 50% to about 90%, preferably from about 60% to about 85% and most preferably from about 70% to about 80% talc.

The talc of the present invention comprises a first talc and a second talc having a ratio of said first talc to said second talc from about 1:1 to about 6:1, preferably from about 2:1 to 4:1, most preferably about 3:1.

While not wishing to be bound by theory, it is believed that using a combination of specifically sized particles promotes the coverage benefits found in the present invention. For example, large or course particle talc contributes towards providing uniformity and spreadability on the skin, however, they do not provide sufficient coverage. On the other hand, smaller or fine particle talc provide good coverage while not providing satisfactory uniformity. Therefore, the key is to combine talcs having particle size distributions or PSD's to form a poly-medal talcs which pack efficiently wherein the fine particles fit within the interstices formed between the larger particles.

As used herein particle size distribution or "PSD" refers to the particle size distribution data obtained by laser diffraction methodology using a Hariba LA-900 particle size analyzer (volume-weighted analysis of distribution). The distribution data are based on the cumulative percent of the particles which are less than a designated micron sizes. In the present invention the first talc being coarse has a PSD wherein no more than about 45%, preferably no more than about 40% and most preferably no more than about 35% of the particles are 10 microns or less; no more than about 70%, preferably no more than about 65% and most preferably no more than about 60% of the particles are 15 microns or less and no more than about 85%, preferably no more than about 80% and most preferably no more than about 75% of the particles are 20 microns or less. The second talc of the present invention being fine has a PSD wherein no less than about 55%, preferably no less than about 60% and most preferably no less than about 65% of the particles are 10 microns or less; no less than about 80%, preferably no less than about 85% and most preferably no less than about 90% of the particles are 15 microns or less and no less than about 90%, preferably no less than about 95% and most preferably 100% of the particles are 20 microns or less.

It is also preferred that the talcs have packed densities from about 0.1 g/cc$^3$ to about 1.5 g/cc$^3$, wherein the packed density of said first talc is greater than the packed density of said second talc. It is more preferred that the packed density of the first talc is from about 0.3 g/cc$^3$ to about 1.2 g/cc$^3$, preferably from about 0.5 g/cc$^3$ to about 0.9g/cc$^3$ and the packed density of the second talc is from about 0.1 g/cc$^3$ to about 0.7g/cc$^3$, preferably from about 0.2g/cc$^3$ to about 0.4g/cc$^3$.

It has also been discovered that the talc used in the present invention is preferably talc that has been treated with hydrophobic material. Said hydrophobic materials are applied to the surface of talc in order to impart hydrophobicity to said talc. Improvements to the composition in terms of skin adhesion and improved binding characteristics are attributable to such treatment. It is preferred that the compositions of the present invention comprises at least about 50% talc treated with hydrophobic materials. The hydrophobic materials used to treat talcs of the present invention include silicones, fatty acids esters, surfactants such as lecithin, polyfluorocarbons, rutile titanium dioxide and other such hydrophobic material are known in the art.

Preferable hydrophobic materials used to treat talcs of the present invention are silicones having a viscosity from about 0.5 to about 20,000 centistokes (csts), preferably from about 1 to about 500 csts, most preferably from about 10 to about 100 csts. Although the silicone material of the present invention may be either volatile or non-volatile, non-volatile materials are preferred. By "non-volatile" it is meant that the vapor pressure of said fluid is less than about 10mm Hg, preferably less than about 1 mm Hg, and most preferably less than about 0.5 mm Hg at 30° C. as measured using analytical means known to those skilled in the art.

Said silicone material of the present invention include poly(organosiloxane) fluids conforming to the formula:

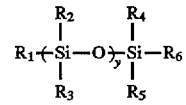

wherein the end groups $R_1$ and $R_6$ are independently selected from the group consisting of hydroxyl groups, lower alkyl groups having carbon chain lengths from about $C_1$ to about $C_6$ and mixtures thereof, preferably methyl groups and the non-end groups $R_2$, $R_3$, $R_4$ and $R_5$ are independently selected from methyl groups, fluoroalkyl groups, phenyl groups and mixtures thereof.

The poly(organosiloxane) fluids with non-end groups ($R_2$, $R_3$, $R_4$ and $R_5$) comprising methyl groups are known in the art and provide the final product with a relatively non-lipohilic character. Commercially available non-volatile silicone fluids having such non-end groups include those available from Dow Corning as the 200 Fluids, and those available from General Electric as SF-96 Series.

Silicone fluids with non-end groups comprising fluoroalkyl groups are also useful herein. It is preferable, however, that the fluorine atom is attached to alkyl groups having a $C_3$ to $C_8$ chain length wherein the fluorine atom is attached to attached to said alkyl group at a point no closer than third carbon atoms from the silicone/carbon bond. Commercially available non-volatile silicone fluids having such non-end groups include those available from Dow Corning as the 1265 Fluid series, and those available from General Electric as the SF-1153 Series, most preferred is the 1265 Fluid Series, most preferably those of having a viscosity from about 100 csts to about 350 csts.

Silicone fluids with the non-end groups comprising allyl groups are also useful in the present invention. The allyl groups which are particularly useful in the present invention are phenyl groups. Particularly useful allyl-substituted silicone fluids commercially available are available as the 556 Series from Dow Corning.

Preferable poly(organosiloxane) fluids of the present invention are selected from the group consisting of perfluoropolyether fluids, poly(dimethylsiloxane) fluids, poly(phenylmethylsiloxane) fluids, poly(fluoroalkylmethylsiloxane) fluids, the copolymers of said fluids and mixtures thereof. More preferred fluids are selected from the group consisting of perfluoropolyether fluids, poly(dimethylsiloxane) fluids, their copolymers and mixtures thereof. Most preferred are poly(dimethylsiloxane) fluids and their copolymers. Said fluids are selected from the group consisting of perfluoropolyether fluids, poly(dimethylsiloxane) fluids, poly(phenylmethylsiloxane) fluids, poly(fluoroalkylmethylsiloxane) fluids, the copolymers of said fluids and mixtures thereof. More preferred fluids are selected from the group consisting of perfluoropolyether fluids, poly(dimethylsiloxane) fluids, their copolymers and mixtures thereof. Most preferred are poly(dimethylsiloxane) fluids and their copolymers, preferably selected from the group consisting of dimethicone, phenyl dimethicone, phenyl trimethicone and mixtures thereof.

The polyfluorocarbon materials useful in the present invention includes perfluoropolyethers of general formula:

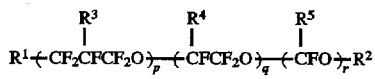

wherein $R^1$ though $R^5$ are independent fluorine atoms, perfluoroalkyl groups, or oxyperfluoroalkyl groups; the value of p, q, and r is at least zero; wherein the perfluoropolyether molecular weight is from about 500 to about 10,000, wherein P, Q and R may be equal, but, not zero. A preferred perfluoropolyether is the commercially available product known as Fomblin HC-04, HC-25, and HC-R available from Montefluosu of Milano, Italy.

Treated talcs of the present invention are available from a number of commercial sources. Said treated talcs include PF-5 Talc, SI Talc, JA-13R and JA-46R, all available from Kobo, South Plainfield N.J.; DF-10240 available from Color Techniques, South Plainfield, N.J.; Sim 2043 available from Ecco Resources, South Plainfield, N.J.; Miki T-Uft-20 and Miki-13-ST available from Miki America, Inc., Dayville, Conn.; and J-68-ST-PEG/MOD available from U.S. Cosmetics Corporation, Dayville, Conn.

Sebum Absorbing Materials

The present invention utilizes sebum absorbing materials in levels necessary to reduce the amount of sebum on the surface of the skin therein providing substantial long wear benefits of the cosmetic composition. To achieve sufficient sebum absorption for increased cosmetic wear the composition comprises from about 2.0% to about 15%, preferably from about 2.0% to about 8.0%, and most preferably from about 2.0% to about 4.0% of a sebum absorbing material capable of absorbing from about 0.2 grams of sebum per gram of material (herein referred to as $g_{sebum}/g_{material}$) to about $3.5g_{sebum}/g_{material}$, preferably from about 0.8 $g_{sebum}/g_{material}$ to about $2.6g_{sebum}/g_{material}$, and most preferably from about $1.5g_{sebum}/g_{material}$ to about $2.0g_{sebum}/g_{material}$. Compositions of the present invention containing such sebum absorbing material are able to absorb from about 0.20g of sebum per gram of the composition (herein referred to as $g_{sebum}/g_{composition}$) to about $0.35g_{sebum}/g_{composition}$, preferably from about $0.25g_{sebum}/g_{composition}$ to about $0.32g_{sebum}/g_{composition}$, and most preferably from about $0.28g_{sebum}/g_{composition}$ to about $0.30g_{sebum}/g_{composition}$.

The method of measuring the absorption of sebum by the sebum absorbing material or composition of the present invention is titration of a sample of said material or composition with the sebum as shown in the formulation below. Conducting the above titration is as follows:

Weigh a 1.0 gram of the sample of said material or composition into a 125 ml. metal beaker. Break up any agglomerates of the sample using a spatula (Note: agglomerates can be found in the sample itself or be formed in the beaker). Mix the sample with a Kitchen Aid™ hand mixer, (model no. KAM 5TBWH-1) equipped with the liquid blender rod illustrated in the mixer's instruction manual, at Setting 1 (lowest setting). Add the sebum to the sample while mixing until the sample is saturated. Saturation of the sample is reached when the sample completely adheres to the liquid blender rod and not to the side of the beaker, when the rotating liquid blender rod is pressed moderately against the side wall of the beaker.

Multiplying the volume of sebum added to one gram of the sample by the density of the sebum (0.870g/ml) provides the grams of sebum per gram of material or composition titrated.

| Sebum Formula | |
|---|---|
| Component | Amount (% by weight) |
| Mazola ™ Corn Oil | 7.30 |
| Squalene | 18.80 |
| Oleic Acid | 28.30 |
| Ceraphyl ™ 140 | 45.60 |

Sebum absorbing materials used in the compositions of the present invention are selected from the group consisting of starch, calcium silicate, polyethylene, nylon, boran nitride, mica, kaolin, polymer powders including natural, synthetic, and semi-synthetic cellulose, fluorocarbon resins, polypropylene, modified starches of cellulose acetate, particulate cross-linked hydrophobic acrylate or methacrylate copolymers and mixtures thereof. The hydrophobic polymer is a highly crosslinked polymer, more particularly a highly cross-linked polymethacrylate copolymer. The material is manufactured by the Dow Corning Corporation, Midland. Michigan, USA, and sold under the trademark POLYTRAP™. Sebum absorbing materials preferred for use in the present invention include starch, calcium silicate, boran nitride and mixtures thereof; most preferably starch.

The starch used in the present invention is defined as a group of carbohydrates or polysaccharides, of the general composition $C_6H_{10}O_5$, occurring as organized or structural granules of varying sizes and markings in many plant cells and hydrolyzable to several forms of dextrin and glucose. The starch found most useful in the present invention is a tapioca dextrin starch. Tapioca refers to the plant from which the starch is derived. Dextrin refers to a process the starch has been subjected to which breaks up the relatively high molecular weight starch to form a more complicated starch structure (amylopectin) which is attracts hydrophobic materials such as sebum. Tapioca dextrin starch is commercially available from The National Starch and Chemical Company as Natrasorb Bath Starch. During processing of Natrasorb Bath Starch, the tapioca dextrin particles which are hollow spheres, are spray dried with ammonium bicarbonate which creates "pock" marks on the starch surface increasing its surface area. This greater increases the surface area, resulting in greater sebum absorption of the starch.

Optional Ingredients

Compositions of the present invention can include numerous cosmetically acceptable ingredients selected for various desirable effects. These ingredients can be either in dry or liquid form, however, at levels that do not detract from the primary objects of the present invention.

Pigments are used in the present invention. Pigments may be selected from a large group of materials to numerous to mention herein. Included in this group are inorganic pigments, organic pigments, and pearlescent pigments. When employed, the pigments are present in proportions depending on the color and the intensity of the color which it is intended to produce. Pigments can be used in the present invention at levels from about 0.1% to about 20%, preferably from about 0.5% to about 12%. Pigments are selected from the group consisting of inorganic pigments, organic lake pigments, pearlesent pigments, and mixtures thereof. Said pigments may optionally be surface-treated with a large number of materials that include, but, not limited to silicones, perfluorinated compounds, lecithin, amino acids, lauroyl lisine, teflon, and esters. Included are the pigments as disclosed in U.S. Pat. Nos. 5,368,639 and 5,458,681, both to Hasegawa et at., issued Nov. 29, 1994 and Oct. 17, 1995; both herein incorporated by reference. Inorganic pigments useful in the present invention include those selected from the group consisting of rutile or anatase titanium dioxide, coded in the Color Index under the reference CI 77,891; black, yellow, red and brown iron oxides, ceded under references CI 77,499, 77,492 and, 77,491; manganese violet (CI 77,742); ultramarine blue (CI 77,007); chromium oxide (CI 77,288); chromium hydrate (CI 77,289); and ferric blue (CI 77,510) and mixtures thereof.

The organic pigments and lakes useful in the present invention include those selected from the group consisting of D&C Red No. 19 (CI 45,170), D&C Red No. 9 (CI 15,585),D&C Red NO. 21 (CI 45,380), D&C Orange No. 4 (CI 15,510), D&C Orange No. 5 (CI 45,370), D&C Red No. 27 (CI 45,410), D&C Red No. 13 (CI 15,630), D&C Red No. 7 (CI 15,850), D&C Red No. 6 (CI 15,850), D&C Yellow No. 5 (CI 19,140), D&C Red No. 36 (CI 12,085), D&C Orange No. 10 (CI 45,425), D&C Yellow No. 6 (CI 15,985), D&C Red No. 30 (CI 73,360), D&C Red No. 3 (CI 45,430) and the dye or lakes based on Cochineal Carmine (CI 75,570) and mixtures thereof.

The pearlescent pigments useful in the present invention include those selected from the group consisting of the white pearlescent pigments such as mica coated with titanium oxide, bismuth oxychloride, colored pearlescent pigments such as titanium mica with iron oxides, titanium mica with ferric blue, chromium oxide and the like, titanium mica with an organic pigment of the above-mentioned type as well as those based on bismuth oxychloride and mixtures thereof.

Any optional ingredients known to those skilled in the art may also be used in the invention. Examples of optional ingredients are disclosed in *CTFA Cosmetic Ingredient Handbook*, Second Edition, 1992, pages 621–622, 623–626 and 637–639; incorporated herein by reference. Some of the more frequently used components include from about 1% to about 10% fillers and powders other than talc, including but not limited to the group consisting of treated and untreated mica, nylon, polyethylene, silica, polymethacrylate., kaolin, teflon, starch, oil absorbers and mixtures thereof. From about 1 to about 20% liquid ingredients including, but not limited to the group consisting of silicone oils; long chained fatty acid esters; glycerides; water; fragrances; skin conditioning and protective materials including, botanical or biological products as disclosed in The CTFA, Cosmetic Ingredient Handbook, Second Edition, pages 493–496; herein incorporated by reference. Other skin conditioning and protective material include, but, are not limited to panthenol, allantoin, aloe, aloe vera gel, PABA, tocopheryl; and mixtures thereof. From about 0.1% to about 2% cosmetic preservatives including, but not limited to the group consisting of methylparaben, propylparaben, butylparaben, ethylparaben, potassium sorbate, trisodium EDTA, phenoxyethanol, ethyl alcohol, diazolidinyl urea, imidazolidinyl urea, quaternium-15 and mixtures thereof.

Coverage Measurement

As stated above, the compositions of the present invention have improved coverage compared with conventional powder compositions known in the art. The following test determines the extent of coverage of the powder composition:

Attach several 8"×14" strips of 100% black cotton fabric to a flat vertical surface. The fabric is model CC SLD 7018, Black, at 44 threads per inch, available from Beachwood Fabric Centers of America. The fabric strips can be cut to 5 ½" lengths once the test is complete, facilitating its display for evaluation.

A new applicator is to be used for each sample tested. In the case of a compressed powder product, the entire surface of the product is first wiped with the applicator for 8–10 strokes until surface of cake is broken or ribbon/design mark has been removed. Twice rub in a circular motion in a circular motion across entire surface of the powder product one half of a cosmetic applicator such as a sponge or puff. In the case of a loose powder, the entire puff is dabbed five times onto the screen over the powder.

Wipe the applicator in a downward motion using even pressure on the applicator to distribute the powder over a six to seven inch length of the material disclosed above. Continue to wipe the applicator over the same area of the material for about nine more times, with no additional replenishment of product to the applicator.

The samples are evaluated for coverage and uniformity, often referred to as "payout" using a Spectraflash 500™ Spectrophotometer made by Datacolor International, Lawrenceville, N.J. The value V is the ratio of K to S wherein K is the value of the light absorbed and S is the value for the light scattered, the light being that having a wavelength of the highest absorption value for the black fabric. The Coverage Value or CV of the sample is determined by dividing value V for the sample by the value V for the fabric. The CV of the sample is compared to standard products known to have either desirable or non-desirable coverage and uniformity characteristics when applied to the skin.

EXAMPLES

The following are non-limiting of powder products which embody the present invention. Said samples contain a number of other routinely used cosmetic ingredients which is envisioned to be used in conjunction with the present invention. Said ingredients are employed to help for the specific product form, and/or to promote secondary skin benefits such as oil control and moisturization.

| Component | Amount (% by weight) |
|---|---|
| 1. Press Powder Foundation | |
| Octyldodecyl Steroyl Stearate | 4.97 |
| Silicone Oil[1] | 2.48 |
| Trimethyl Trimellitate | 0.80 |
| Talc | |
| Talc One[2] | 52.06 |
| Talc Two[3] | 19.26 |
| Zinc Stearate | 1.40 |
| Calcium Silicate | 1.80 |
| Nylon-12 | 1.60 |
| Silica | 0.50 |
| Bismuth Oxychloride | 2.00 |
| Starch[4] | 3.00 |
| Methylparaben | 0.20 |
| Propylparaben | 0.10 |
| Sodium Dehydroacetate Monohydrate | 0.12 |
| Pigments | |
| Treated Yellow Iron Oxide | 0.70 |
| Treated Red Iron Oxide | 0.59 |
| Treated Black Iron Oxide | 0.36 |
| Treated Mica | 5.00 |
| Ultramarine Blue | 0.06 |
| Titanium Dioxide | 3.00 |

[1]available from Dow Corning as DC 200 Fluid
[2]available from US Cosmetics as J-68-ST-PEG/MOD
[3]available from US Cosmetics as Miki-13-ST
[4]available from The National Starch and Chen-Lical as Natrasorb

| Component | Amount (% by weight) |
|---|---|
| 2. Loose Powder | |
| Octyldodecyl Steroyl Stearate | 3.61 |
| Silicone Oil | 1.81 |
| Trimethyl Trimellitate | 0.58 |
| Talc | |
| Talc One[2] | 37.51 |
| Talc Two[3] | 25.00 |
| Zinc Stearate | 1.50 |
| Magnesium Carbonate | 3.50 |
| Polyethylene | 3.35 |
| Sericite | 10.00 |
| Calcium Silicate | 1.50 |
| Starch[4] | 2.25 |
| Methylparaben | 0.20 |
| Propylparaben | 0.10 |
| Sodium Dehydroacetate Monohydrate | 0.10 |
| Quaternium-15 | 0.02 |
| Pigments | |
| Treated Yellow Iron Oxide | 0.48 |
| Treated Red Iron Oxide | 0.25 |
| Treated Black Iron Oxide | 0.24 |
| Treated Mica | 5.00 |
| Titanium Dioxide | 3.00 |

[1]available from Dow Corning as DC 200 Fluid
[2]available from Color Techniques as DF-10240
[3]available from Kobo as A-CL3
[4]available from Cosmetic Speciallies as Buffalo Starch

| Component | Amount (% by weight) |
|---|---|
| 3. Pressed Powder | |
| Octyldodecyl Steroyl Stearate | 0.50 |
| Silicone Oil[1] | 3.50 |
| Dimethicone and Trimethysiloxsilicate | 2.75 |
| $C_{12}$-$C_{15}$ Alkyl Benzoate | 0.50 |
| Coco-Capryiate/Caprate | 2.20 |
| Talc | |
| Talc One[2] | 45.50 |
| Talc Two[3] | 19.50 |
| Zinc Stearate | 2.50 |
| Polyethylene | 3.00 |
| Kaolin | 2.00 |
| Starch[4] | 5.00 |
| Methylparaben | 0.20 |
| Propylparaben | 0.10 |
| Ethylparaben | 0.10 |
| Pigments | |
| Treated Yellow Iron Oxide | 0.80 |
| Treated Red iron Oxide | 0.31 |
| Treated Black iron Oxide | 0.14 |
| Treated Mica | 10.00 |
| Titanium Dioxide | 1.40 |

[1]available from Dow Corning as DC 200 Fluid
[2]available from US Cosmetics as Soft Talc
[3]available from US Cosmetics as LI TA 13R
[4]available from The National Starch and Chemical as Dry Flo

| Component | Amount (% by weight) |
|---|---|
| 4. Pressed Powder | |
| Octyldodecyl Steroyl Stearate | 5.00 |
| Silicone Oil | 1.00 |
| Talc | |
| Talc One[2] | 48.30 |
| Talc Two[3] | 20.45 |
| Zinc Stearate | 2.50 |
| Polyethylene | 3.00 |
| Calcium Silicate | 1.00 |
| Micro Sponge Powder[4] | 4.00 |
| Botanical Oil[5] | 2.00 |
| Methylparaben | 0.20 |
| Propylparaben | 0.10 |
| Imidazolidinyl Urea | 0.10 |
| Pigments | |
| Treated Yellow Iron Oxide | 0.11 |
| Treated Red Iron Oxide | 0.80 |
| Treated Black Iron Oxide | 0.02 |
| Treated Utramarine Blue | 0.02 |
| Treated Mica | 10.00 |
| Titanium Dioxide | 1.40 |

[1]available from Dow Corning as SF-96-350 type
[2]available from US Cosmetics as Soft Talc
[3]available from US Cosmetics as LI TA 13R
[4]available from Dow Corning as Polytrap
[5]available from Bush Boake Allen, as Essential Oil 103-06.

Process Method

Mix all the powdery or dry materials in powder blender, such as a Lodige mixer until homogeneous. Pulverize this mixture in a standard hammer mill, such as Micropul single hammer mill, equipped with a 0.010" herringbone screen. Return the mixture to the powder blender. Mix at ambient temperature all the liquid ingredients in a vessel equipped with a mixer, such as a Lighting Mixer until homogeneous. Spray the liquid mixture onto the powdery mixture in the powder blender and mix about 10 minutes. Stop the powder blender, scrape side walls and mix for about 5 minutes. Sift the resulting granulation through a 0.032" screen and place into storage bins. In the case of pressed powders, compress the granulation into various shaped standard makeup pans or godets using a ribbon punch press, such as a Hydraulic Kemwall Press, at a compression pressure wherein the pressed powder can sustain physical insult when exposed to routine quality testing such as a drop test which is routinely used in the art. Insert the pans in appropriate cosmetic cases.

In the case of loose powders, appropriate canisters are filled with the granulation from the storage bins using for example a volumetric filler such as Master or All-fill feeders.

We claim:

1. A powder cosmetic composition comprising talc wherein said talc comprises:

a. a first talc having a particle size distribution wherein no more than about 45% of the particles are 10 microns or less, no more than about 70% of the particles are 15 microns or less and no more than about 85% of the particles are 20 microns or less;

b. a second talc having a particle size distribution wherein no less than about 55% of the particles are 10 microns or less, no less than about 80% of the particles are 15 microns or less and no less than about 90% of the particles are 20 microns or less;

wherein the ratio of said first talc to said second talc is from about 1:1 to about 6:1; and c. a sufficient amount of an sebum absorbing material capable of absorbing from about 0.2 grams of sebum per gram of material ($g_{sebum}/g_{material}$) to about $3.5 g_{sebum}/g_{material}$.

2. A powder cosmetic composition according to claim 1 wherein the first and second talc have packed densities from about 0.1 g./cm3 to about 1.5 g/cm wherein the packed density of said first talc is greater than the packed density of said second talc.

3. A powder cosmetic composition according to claim 2 comprising:

a. from about 50% to about 90% talc; and b. from about 2.0% to about 15% sebum absorbing material.

4. A powder cosmetic composition comprising talc wherein said talc comprises:

a. a first talc having a particle size distribution wherein no more than about 40% of the particles are 10 microns or less; no more than about 65% of the particles are 15 microns or less and no more than about 80% of the particles are 20 microns or less;

b. a second talc having a particle size distribution wherein no less than about 60% of the particles are 10 microns or less, no less than about 85% of the particles are 15 microns or less and no less than about 95% of the particles are 20 microns or less;

wherein the ratio of said first talc to said second talc is from about from about 2:1 to 4:1; and c. a sufficient amount of an sebum absorbing material capable of absorbing from about 0.8 grams of sebum per gram of material ($g_{sebum}/g_{material}$) to about $2.6 g_{sebum}/g_{material}$.

5. A powder cosmetic composition according to claim 4 wherein the first talc has a packed density is from about 0.3g/cm3 to about 1.2 g/cm3 and the second talc has a packed density from about 0.1 g/cm3 to about 0.7 g/cm3 wherein the packed density of said first talc is greater than the packed density of said second talc.

6. A powder cosmetic composition according to claim 4 comprising:

a. from about 60% to about 85% talc; and b. from about 2.0% to about 8.0% sebum absorbing material.

7. A powder cosmetic composition comprising talc wherein said talc comprises:

a. a first talc having a particle size distribution wherein no more than about 35% of the particles are 10 microns or less, no more than about 60% of the particles are 15 microns or less and no more than about 75% of the particles are 20 microns or less;

b. a second talc having a particle size distribution wherein no less than about 65% of the particles are 10 microns or less, no less than about 90% of the particles are 15 microns or less and no less than about 100% of the particles are 20 microns or less;

wherein the ratio of said first talc to said second talc is from about from about 3:1; and c. a sufficient amount of an sebum absorbing material capable of absorbing from about 1.5 grams of sebum per gram of material ($g_{sebum}/g_{material}$) to about $2.0 g_{sebum}/g_{material}$.

8. A powder cosmetic composition according to claim 7 wherein said composition comprises:

a. from about 70% to about 80% talc; and b. from about 2.0% to about 4.0% sebum absorbing material.

9. A powder cosmetic composition according to claim 8 wherein the first talc has a packed density is from about 0.5/cm3 to about 0.9 g/cm3 and the second talc has a packed density from about 0.2 g/cm3 to about 0.4 g/cm3 wherein the packed density of said first talc is greater than the packed density of said second talc.

10. A powder cosmetic composition according to claim 9 wherein the composition comprises at least about 50% talc treated with hydrophobic material.

11. A powder cosmetic composition according to claim 10 wherein the hydrophobic material is selected from the group consisting of silicone, fatty acid esters, lecithin, polyfluorocarbons, rutile titanium dioxide and mixtures thereof.

12. A powder cosmetic composition according to claim 11 wherein the hydrophobic material is silicone.

13. A powder cosmetic composition according to claim 12 wherein the silicone is a poly(organosiloxane) fluids conforming to the formula:

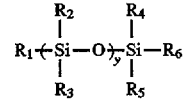

wherein the end groups $R_1$ and $R_6$ are independently selected from the group consisting of hydroxyl groups, lower alkyl groups having carbon chain lengths from about $C_1$ to about $C_6$ and mixtures thereof and the non-end groups $R_2$, $R_3$, $R_4$ and $R_5$ are independently selected from methyl groups, fluoroalkyl groups, phenyl groups and mixtures thereof.

14. A powder cosmetic composition according to claim 13 wherein the end groups $R_1$ and $R_6$ are methyl groups.

15. A powder cosmetic composition according to claim 1 wherein the sebum absorbing material is selected from the group consisting of starch, calcium silicate, polyethylene, nylon, boran nitride, mica, kaolin, polymer powders including natural, synthetic, and semi-synthetic cellulose, fluorocarbon resins, polypropylene, modified starches of cellulose acetate, particulate cross-linked hydrophobic acrylate or methacrylate copolymers and mixtures thereof.

16. A powder cosmetic composition according to claim 15 wherein the sebum absorbing material is selected from the group consisting of starch, calcium silicate, polyethylene, nylon, boran nitride and mixtures thereof.

17. A powder cosmetic composition according to claim 16 wherein the starch is a tapioca dextrin starch.

18. A pressed powder composition according to claim 17 further comprising:

a. from about 0.5% to about 12% pigment;

b. from about 1% to about 10% filler material;

c. from about 1% to about 20% liquid material; and d. from about 0.1% to about 2% preservative.

19. A pressed powder composition according to claim 18 wherein the filler material is selected from the group consisting of treated and untreated mica, nylon, polyethylene, silica, polymethacrylate, kaolin, teflon, and mixtures thereof.

20. A pressed powder composition according to claim 18 wherein the cosmetic preservatives are selected from the group consisting of methylparaben, propylparaben, butylparaben, ethylparaben, potassium sorbate, trisodium EDTA, phenoxyethanol, ethyl alcohol, diazolidinyl urea, imidazolidinyl urea, quaternium-15 and mixtures thereof.

* * * * *

UNITED STATES PATENT AND TRADEMARK OFFICE
CERTIFICATE OF CORRECTION

PATENT NO. : 5,683,706
DATED : November 4, 1997
INVENTOR(S) : PATRICIA A. LAFLEUR, et al.

It is certified that error appears in the above-identified patent and that said Letters Patent is hereby corrected as shown below:

Column 9, line 12 "1,80" should read --1.80--.

Column 9, line 59 "2,75" should read --2.75--.

Column 10, line 5 "0.1,0" should read --0.10--.

Column 10, line 9 "0,31" should read --0.31--.

Signed and Sealed this

Twenty-fourth Day of February, 1998

Attest:

BRUCE LEHMAN

*Attesting Officer*      *Commissioner of Patents and Trademarks*